(12) United States Patent
Andersson et al.

(10) Patent No.: US 6,306,433 B1
(45) Date of Patent: *Oct. 23, 2001

(54) METHOD OF PREPARING PHARMACEUTICAL COMPOSITIONS

(75) Inventors: Mattias Andersson, Täby; Dorota Johansson, Huddinge; Percy Li, Hässelby; Björn Norrlind, Stockholm; Bengt Westgren, Vällingby, all of (SE)

(73) Assignee: Pharmacia AB, Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,606

(22) Filed: Jul. 22, 1998

Related U.S. Application Data (60) Provisional application No. 60/055,139, filed on Aug. 12, 1997.

(51) Int. Cl.⁷ .................................................. A61K 9/127
(52) U.S. Cl. .............................................................. 424/450
(58) Field of Search ............................. 424/450; 264/4.1, 264/4.3, 4.6; 514/2, 21, 824

(56) References Cited

U.S. PATENT DOCUMENTS

| 4,643,988 | 2/1987 | Segrest et al. . |
| 5,128,318 | 7/1992 | Levine et al. . |
| 5,662,932 | 9/1997 | Amselem et al. . |
| 5,665,379 | 9/1997 | Herslöf et al. . |
| 5,817,856 | * 10/1998 | Tirosh .................................. 558/169 |

FOREIGN PATENT DOCUMENTS

| 2138925 | 1/1995 | (CA) . |
| 0 663407A1 | 7/1995 | (DE) . |
| 61-152632 | 7/1986 | (JP) . |
| 0353267 B1 | 2/1990 | (SE) . |
| WO 87/02062 | 4/1987 | (WO) . |
| WO 93/06921 | 4/1993 | (WO) . |
| WO 93/12143 | 6/1993 | (WO) . |
| WO 94/13819 | 6/1994 | (WO) . |
| WO 98/07751 | 2/1998 | (WO) . |

OTHER PUBLICATIONS

*Journal of Pharmaceutical Sciences,* Lo et al., 84(7), pp. 805–814 (1995).
*Principles of Biochemistry: Mammalian Biochemistry.,* E.L. Smith et al., 7th Ed., pp. 268–277.
*Advanced Drug Delivery Reviews,* Rodrigueza et al., 32, pp. 31–43 (1998).
*Liposome Technology,* Brandl et al., vol. 1, pp. 50–64 (1993).
*Immunomethods,* Alan L. Weiner, 4, pp. 201–209 (1994).
*Experimental Lung Research,* Ana Jonas, 6, pp. 255–270 (1984).
*Journal of Bio. Chemistry,* Franceschini et al., vol. 260 (30), pp. 16321–16325 (1985).

* cited by examiner

Primary Examiner—Gollamudi S. Kishore
(74) Attorney, Agent, or Firm—Gilberto M. Villacorta; Corine M. Pouliquen; Pepper Hamilton LLP

(57) ABSTRACT

The invention relates to a method of preparing a composition of lipid particles comprising a bioactive protein, capable of being subjected to high shear forces without substantial loss of activity, and a lipid agent. The characterizing features of the method are the introduction of a protein preparation and a lipid agent to a homogenization station, whereupon the resulting fluid mixture of protein an lipid agent is subjected to high pressure homogenization. The so formed lipid particles are collected and if necessary further processed into a pharmaceutical formulation.

41 Claims, 6 Drawing Sheets

METHOD OF PREPARING PHARMACEUTICAL COMPOSITIONS

RELATED APPLICATIONS

This application claims priority from Swedish Patent Application No. SE 9702776-7 filed Jul. 22, 1997 and U.S. Provisional Application No. 60/055,139 filed Aug. 12, 1997, both of which are incorporated herein by reference.

FIELD OF INVENTION

The present invention relates to a method for the preparation of pharmaceutical compositions of proteins and lipids by means of high pressure homogenization, as well as pharmaceutical compositions obtainable by the process.

BACKGROUND OF INVENTION

It is considered a demanding problem to define and develop a method for preparing a composition of a protein with pharmaceutical properties, suitable for large scale pharmaceutical production and resulting in a safe, efficient and clinically acceptable pharmaceutical product. One problem is to retain the stability of the protein during preparation, storage and handling. Another problem is to assure the desired pharmacokinetic and pharmacodynamic properties of the protein. It has frequently been suggested that dispersed lipid systems would constitute suitable carriers for pharmaceuticals including proteins and the mentioned problems are in many aspects the same also for such dispersed systems. It would therefore be desirable to be able to provide a method of linking proteins and lipids and thereby overcoming the mentioned problems which is many cases also relates to the dispersed lipids. In particular, it would be desirable to be able to associate the protein with a lipid carrier for improving the protein stability and the provision of a specifically designed drug delivery formulations. In certain applications, it would for example also be desirable to extend the in-vivo half life in the circulation system of the bioactive protein which otherwise risks to be enzymatically degraded before reaching the target where it should exert its beneficial activity.

A lot of efforts has been devoted in finding such suitable administration forms which maintain the bioactivity of the protein, while at the same time avoiding the involvement of carriers and formulation adjuvants which can cause clinical side-effects. Imitations of the native lipid-protein transport particles in the blood stream have been suggested as one attractive model for designing administration systems for bioactive proteins. Some important forms of these lipid particles are chylomicrons, the transporters of triglycerides which appear in the blood stream after ingestion of lipid rich food, VLDL, LDL- and HDL-particles. These particles are mainly composed of free and esterified cholesterol, triglycerides, phospholipids and several other minor lipid components and proteins. The LDL-particles serve as transporters of cholesterol and other lipids to the cells, while the HDL-particles transport these materials to the liver for elimination. A HDL particle frequently has a disc-shaped form with an outer surface covered by a phospholipid layer and a hydrophobic core. Amphiphilic proteins, such as apolipoprotein A-I and A-II are attached to the surface by means of interaction of the hydrophobic face of their alpha helical domain with the hydrophobic part of the phospholipids.

Synthetic chylomicron-like products have particularly found use as parenteral nutrients. It is a widely established technology to prepare lipid emulsions from a purified triglyceridic oil (predominantly soybean and safflower oil) and phospholipids (from egg yolk or soybeans) which are regarded as clinically acceptable for parenteral use due to their chylomicron-like emulsion droplets, generally of the size between 0.1 to 1 µm. There also exist several commercial products where such emulsions are used as carriers for lipophilic drugs which are dissolved in the dispersed lipid phase, such as Diazemuls® and Diprivan®. However, a practical complication with this type of emulsion carriers is their relative physical instability which frequently is impaired by the addition of the hydrophobic drug and lead to a break-up of the emulsion and thus making it dangerous to administer because of the risk of lipid embolism. There have been many attempts to solve this problem by adding stabilizers which, however, often are connected with undesired side-effects. The liability of such emulsions, also in connection with sterilization by high pressure steam, i.e. autoclavation and during subsequent storage, have often inhibited their use as drug parenteral drug carriers. Generally, autoclavation procedures also tend to damage many labile pharmaceuticals to be incorporated with emulsions as for example many proteins.

Liposomes have frequently been suggested as suitable vehicles for parenteral protein delivery, as for example disclosed in the article by A L Weiner in Immunomethods, 1994, Vol. 4, pp. 201–209. A liposome carrier would for example be advantageous when an improved solubilization, a sustained release (or extended half-life) or an improved targeting of the protein are desired. It is, however, acknowledged in the mentioned article that many frequently methods used to design liposomal systems often involve procedures which risk to destroy the activity of sensitive proteins, for example by denaturation and oxidation. Moreover, in Liposome Technology, 1993 by CRC Press Inc., Vol. 1, Ch. 3, pp. 49–63: M M Brandl et al, it is disclosed how to utilize high pressure homogenization for preparing liposomes of small unilamellar quality and suitability of this technique for the reduction of vesicle size, broadness of size distribution and lamellarity of preformed multilamellar vesicle dispersions. Also the entrapment of proteins and peptides, specifically hemoglobin and insulin, is disclosed, however, the small size of the resulting vesicles is disadvantageous and the entrapment efficiencies of the proteins are low. Moreover, it is reported that the integrity and the biological function of hemoglobin is maintained, at least during short exposures to stressing conditions.

Another type of delivery system of a dispersed lipid agent which is suggested as suitable for proteins is disclosed in WO 93/06921. This system comprises colloidal lipid particles having an interior non-lamellar phase of lipids such as a reversed hexagonal phase or cubic phase which may be associated with a protein.

On the other hand, many proteins in purified form are notoriously difficult to formulate. For example, human growth hormone (hGH) exhibits poor stability in aqueous solution during storage for which reason it is advised to store preparations in a lyophilized form until its administration when it is reconstituted to an injectible solution. However, an inadvertent exposure to shear forces due to a careless reconstitution process will irrevocably lead to a loss of biological activity. For this reason especially designed means for performing a gentle reconstitution have been developed for human growth hormone as disclosed in EP 0 298 067.

There are many disclosures of synthetic HDL-particles in the literature which refer to their capacity in picking up and removing undesired lipid material in the blood stream and from the blood vessels thus making them potentially useful in therapy for treating atherosclerosis by depleting cholesterol from arterial plaques and for removing lipid soluble toxins such as endotoxins.

In Experimental Lung Res. 1984, Vol. 6, pp. 255–270: A Jonas, experimental conditions of forming complexes of the partially hydrophobic apolipoproteins and phospholipids are described in detail. It was found that, by contacting apolipoproteins with preformed phosphatidyl choline vesicles, lipid particles were spontaneously formed which could be used as analogs of HDL-particles. By mixing phosphatidyl choline and bile acids to a miscellar dispersion and contacting the resultant mixture with apolipoproteins specifically shaped, discoidal and thermodynamically stable lipid particles were formed by means of a dialysis method, subsequently called the "cholate-dialysis method".

U.S. Pat. No. 4,643,988 to Research Corporation describes synthetic peptides useful in treatment of atherosclerosis with an improved amphiphatic helix and an ability to spontaneously form stable discoidal lipid particles with phospholipids which resemble native HDL-complexes. The lipid particles can be formed by contacting vesicles of phosphatidyl choline made by sonication. However, such a production method including sonication is suitable only for smaller batches of lipid particles and not for large scale pharmaceutical production.

U.S. Pat. No. 5,128,318 to Rogosin Institute describes the production of reconstituted lipoprotein containing particles (HDL-particles) from plasma derived apolipoproteins which are processed to synthetic particles for parenteral administration with the addition of cholate and egg yolk phosphatidyl choline. A similar method is also disclosed in the Japanese patent application JP 61-152632 to Daiichi Seiyaku KK.

Also in WO 87/02062 to Biotechn. Res. Partners LTD, it is disclosed how to obtain a stabilized formulation by incubating a solution of recombinantly produced lipid binding protein, such as human apolipoprotein, with a conventional lipid emulsion for parenteral nutrition.

The article by G. Franceschini et al. in J. Biol. Chem., 1985, Vol. 260 (30), pp. 16231–25 considers the spontaneous formation of lipid particles between apolipoprotein A-I and phosphatidyl choline. In this article, it is also revealed that Apo-IM (Milano), the variant of apolipoprotein A-I carried by individuals shown to have a very low prevalence of atherosclerosis, has a higher affinity (association rate) to dimyristoyl phosphatidyl choline (DMPC) than regular Apo A-I. It is suggested that the mutant Apo A-IM has a slightly higher exposure of hydrophobic residues which may contribute both an accelerated catabolism and an improved tissue lipid uptake capacity of such Apo A-IM/DMPC particles.

The Canadian patent application CA 2138925 to the Swiss Red Cross discloses an improved, more industrially applicable, method of producing synthetic reconstituted high density lipoprotein (rHDL) particles from purified serum apolipoproteins and phospholipids which avoids organic solvents while resulting in less unbound, free non-complexed phospholipids (i.e. a higher yield of lipoprotein particles). Herein, it is suggested to mix an aqueous solution of apolipoproteins with an aqueous solution of phospholipid and bile acids, whereupon the resultant mixture is incubated and protein-phospholipid particles are spontaneously formed when bile acids are removed from phospholipid/bile acid micelles with diafiltration.

The method employing the use of bile acids for making a micellar dispersion of the lipid according to the cholate-dialysis method have several drawbacks for lipid particle production, since it requires a specific separation step from the resultant mixture. Additionally bile acid residues may even in small amounts be suspected to induce side-effects after parenteral administration and may also constitute a risk of viral contamination. Moreover, the methods referred to above for preparing lipoprotein-lipid particles generally suffer from poor reproducibility and non-definable particle sizes. In particular, none of these methods are suitable in large-scale industrial process under well-controlled conditions.

A surprisingly advantageous method is demonstrated by the present invention which meets these requirements and solve numerous problems which otherwise are associated with protein formulation, especially in large-scale production.

DESCRIPTION OF THE INVENTION

It is an object of the present invention to provide a method for large-scale production of protein-lipid complexes which simply and economically results in lipid particle products in high yield, thus forming a composition with essentially maintained bioactivity of the protein which readily can be transformed into a formulation suitable for therapeutic utility, especially for parenteral administration, to the largest possible extent without employing any such additives which may have potential side-effects in therapy.

It is also an object of the present invention to provide a versatile method which could form a selected category of lipid particles comprising a bioactive protein, suitable for a large number of proteins and designated suitable lipid agents, in a simple manner possible to integrate with the existing or regular downstream processing of recombinant protein production.

It is another object of the present invention to provide a manufacturing process for protein-lipid complexes in the form of lipid particles which avoids subjecting the proteins to treatments leading to the loss of their bioactivity due to excessive temperatures, pH alterations which might inflict denaturation, aggregation or precipitation.

It is still another object of the present invention to provide a manufacturing process for protein-lipid complexes in the form of lipid particles after which the protein maintains its chemical identity due to oxidation of sensitive amino acids like methionine and cysteine and deamidation.

It is further object of the present invention to provide a process for preparing lipid particles comprising a bioactive protein which has a high yield, thus avoiding remnants of large amounts of free proteins and free lipid.

It is a still further object of the present invention to provide a process for large-scale production of lipid particles comprising a bioactive protein that results in composition which readily can be transformed into a pharmacological product, for example in the form of a freeze-dried formulation.

It is a yet further object of the present invention to enable a process resulting in a pharmacologic product of lipid particles and a bioactive protein providing improved aseptic conditions without introducing sterilization methods which risks to destroy a labile protein.

Another object of the present invention is provide a process which can stabilize and modify lipid particles in a lipid dispersion by associating them with a suitable protein.

These objects of invention are attained by the inventive method directed to the preparation of a composition of lipid particles comprising a protein which is capable of being subjected to high shear forces without substantial loss of activity, and a lipid. The inventive method is generally characterized by the steps of introducing an protein preparation and a lipid agent to a homogenization station; subjecting the resultant mixture of protein and the lipid agent together to a high pressure homogenization; and finally collecting the so formed composition of lipid particles.

In addition, the present invention is also directed to a solid composition of a bioactive protein obtainable by the inventive method as well as a kit-of-parts containing such a solid composition and an aqueous reconstitution fluid.

Further details of the methods, the components forming the lipid particle and other process aids constituting different embodiments of the present invention are given below in the appended claims and in the detailed description of the invention.

DETAILED DESCRIPTION OF THE INVENTION

The present invention, in its most general form, is directed to a method of preparing a composition of lipid particles comprising a protein, capable of being subjected to high shear forces without substantial loss of activity, and a lipid agent. The characterizing features of the method are the introduction of a protein preparation and a lipid agent to a homogenization station, whereupon the resulting fluid mixture of protein and lipid agent is subjected to high pressure homogenization. The so formed lipid particles are collected for an optional further processing into a pharmaceutical formulation.

The protein preparation is preferably an aqueous solution of the protein and can be obtained from downstream processing after recombinant production or any other source of protein production and may comprise varying concentrations of protein with varying purity of the desired bioactive protein. Alternatively, the protein preparation is in solid form, such as a conventional lyophilized composition. The protein preparation may simply be introduced separately from lipid into a homogenization station, for example, by separate conduits, to a running homogenization equipment.

It is to be understood that various combinations of protein preparation and lipid agent resulting in a fluid mixture are conceivable to introduce to the homogenization station in accordance with the inventive method. The protein can be introduced to the homogenization station both as an aqueous solution or as lyophilized solid preparation, whereas the lipid agent can be in the form of an aqueous solution or be dissolved in an organic solvent. The lipid agent may also in the form of a dispersion of a lipid in aqueous solvent or be, at least partially in solid form. It is a prerequisite that any such combinations of protein preparation and lipid agent must result in homogenizable fluid and that any utilized organ solvent must be removable with efficient methods not interfering with the clinical requirements of the subsequent product.

In certain applications it is preferred that the protein preparation and the lipid agent are mixed to a homogeneous dispersion or solution before it is subjected to the high shear forces of a high pressure homogenization. It is to be understood that the premixing treatment according to the present invention can be extended to minimize the exposure of the protein to the homogenization treatment in cases when the protein is sensitive (i.e. loss of bioactivity) for extended exposure to the high shear forces during the homogenization. For the same reason, an incubation step optionally can be introduced between the premixing and the homogenization. Alternatively, the premixing is extended to minimize extended homogenization for reasons of process economy. It is to be understood that the premixing can be performed in the same container as the homogenization is performed or in a separate station before being introduced to the homogenization station.

The lipid agent can, at least partially, be in a solid form providing a dispersion with the aqueous solution of protein. For example, a powder-formed lipid can be mixed to a homogenous dispersion before the homogenization with a conventional mixing equipment, while, on the other hand in many applications the powder formed or partially powder formed lipid agent can be introduced directly to the homogenization station.

In the present application lipid is defined as a general term for natural or synthetic compounds consisting of acyl group carriers, such as glycerol, sphingosine, cholesterol and others, to which one or more fatty acids are or could be linked. Also similar molecules that contain a substantial hydrocarbon portion may be included.

The lipid agents used in the present invention can classified into different lipid classes dependent on their polarity:

Nonpolar lipids with polar head groups. Examples of such nonpolar lipids are hydrocarbons or non-swelling amphiphiles, such as mono- , di- or triacylglycerols (glycerides), alkyl esters of fatty acids, fatty alcohols or cholesterol esters.

Polar lipids have polar head groups and exhibit surface activity, such as phospholipids and glycolipids. Dependent on their specific interactions with water they are further subdivided into the categories of swelling and soluble amphiphiles.

Amphipathic or amphiphilic lipids are surface active and exemplified by phospholipids and glycolipids.

Polar lipids are often able to swell in the presence of water to form lipid-crystalline phases, in a structure with short range disorder and long range disorder. There are several different liquids crystalline phases. Many biological lipids such as phosphatidyl choline (PC), phosphatidyl inositol (PI) and sphingomyelin can form bilayer structures, provided that the molecules in question are roughly cylindrical in dimension. However it is also true that many major lipid components of biological systems do not form bilayer structures when isolated and placed in aqueous systems. This has been explained by the fact that the lipid molecules have a shape of a cone or an inverted cone, and thus micellar or inverted micellar structures can be observed. Several cubic lipid-water systems of amphiphilic lipids have also been observed and there are indication of important biological functions of these lipid-water systems.

According to the present invention, the lipid agent comprises an amphiphilic lipid which is capable of forming discrete lipid particles in an aqueous medium, together with the protein, or independently of the presence of the protein, after being subjected to a high pressure homogenization.

The lipid particles generally are stabilized by the polar lipids and their morphology will vary considerably due to the nature of the protein and the lipid agent, as well as the relative amounts of these basic constituents. The present invention is suitable in producing lipid particles having a liposomal (bilayered) structure, lipid particles having the structure of an oil drop in oil-in-water emulsion, or discoidal complexes between a lipoprotein and a phospholipid, as well as other systems of discrete lipid particles stabilized in an aqueous solution, such as micelles, microemulsions, nonoparticles and dispersed hexagonal phases.

In accordance with the present invention it is preferred that the lipid agent comprises an amphiphilic agent. More preferably, the amphiphilic agent is capable of bilayer formation, e.g. a liposome membrane, in an aqueous medium and is selected among at least one of the compounds of the group of phospholipids, glycolipids and cholesterols. Suitable glycolipids are palmitoyl, stearyl or myristoyl glycosides, cholesteryl maltoside, cholesteryl glycoside, various gangliosides and the like. Example of cholesterols are cholesterol, cholesterol acetate, dihydrocholesterol, phytosterol, sitosterol and the like.

In the present invention, the preferred amphiphilic agents are phospholipids which can be of natural origin, such as egg yolk or soybean phospholipids, or synthetic or semisynthetic origin. The phospholipids can be partially purified or fractionated to comprise pure fractions or mixtures of phosphatidyl cholines, phosphatidyl ethanolamines, phosphatidyl inositols, phosphatidic acids, phosphatidyl serines, sphingomyelin or phosphatidyl glycerols. According to specific embodiments of the present invention it is preferred to select phospholipids with defined fatty acid radicals, such as dipalmitoyl phosphatidyl choline, dioleylphosphatidyl choline, dimyristoyl phosphatidyl choline, distearoyl phosphatidyl choline, oleylpalmitoyl phosphatidyl choline and the like phosphatidyl cholines with defined acyl groups selected from naturally occurring fatty acids, generally having 8 to 22 carbon atoms. According to a specific embodiment of the present invention phosphatidyl cholines having only saturated fatty acid residues between 14 and 18 carbon atoms are preferred, and of those dipalmitoyl phosphatidyl choline is especially preferred.

Besides the amphiphilic agent, the lipid agent may comprise, in various amounts at least one nonpolar component which can be selected among pharmaceutical acceptable oils (triglycerides) exemplified by the commonly employed vegetabilic oils such as soybean oil, safflower oil, olive oil, sesame oil, borage oil, castor oil and cottonseed oil or oils from other sources like mineral oils or marine oils including hydrogenated and/or fractionated triglycerides from such sources. Also medium chain triglycerides (MCT-oils, e.g. Miglyol®), and various synthetic or semisynthetic mono-, di- or triglycerides, such as the defined nonpolar lipids disclosed in WO 92/05571 may be used in the present invention as well as acctylated monoglycerides, or alkyl esters of fatty acids, such isopropyl myristate, ethyl oleate (see EP 0 353 267) or fatty acid alcohols, such as oleyl alcohol, cetyl alcohol or various nonpolar derivatives of cholesterol, such as cholesterol esters.

One or more complementary surface active agent can be added to the lipid agent in this invention, for example as complements to the characteristics of amphiphilic agent or to improve its lipid particle stabilizing capacity or enable an improved solubilization of the protein. Such complementary agents can be pharmaceutically acceptable non-ionic surfactants which preferably are alkylene oxide derivatives of an organic compound which contains one or more hydroxylic groups. For example ethoxylated and/or propoxylated alcohol or ester compounds or mixtures thereof are commonly available and are well known as such complements to those skilled in the art. Examples of such compounds are esters of sorbitol and fatty acids, such as sorbitan monopalmitate or sorbitan monopalmitate, oily sucrose esters, polyoxyethylene sorbitane fatty acid esters, polyoxyethylene sorbitol fatty acid esters, polyoxyethylene fatty acid esters, polyoxyethylene alkyl ethers, polyoxyethylene sterol ethers, polyoxyethylene-polypropoxy alkyl ethers, block polymers and cethyl ether, as well as polyoxyethylene castor oil or hydrogenated castor oil derivatives and polyglycerine fatty acid esters. Suitable non-ionic surfactants, include, but are not limited to various grades of Pluronic®, Poloxamer®, Span®, Tween®, Polysorbate®, Tyloxapol®, Emulphor® or Cremophor® and the like. The complementary surface active agents may also be of an ionic nature, such as bile duct agents, cholic acid or deoxycholic their salts and derivatives or free fatty acids, such as oleic acid, linoleic acid and others. Other ionic surface active agents are found among cationic lipids like C10–C24: alkylamines or alkanolamine and cationic cholesterol esters.

Also other pharmacologically acceptable components can be added to the lipid agent when desired, such as antioxidants (exemplified by alpha-tocopherol) and solubilization adjuvants (exemplified by benzylalcohol).

As indicated above, the lipid agent preferably already is formulated and mixed before it is contacted with the protein solution in the premixing step or directly in the homogenization station. However, it is also conceivable within the scope of the invention to successively add one or more constituents of the lipid agent and/or protein step-wise or successively during these two processes.

According to the present invention the characteristics of the protein-lipid particles formed will vary to a large extent dependent on the composition of lipid agent and particularly on the relationship between polar and nonpolar lipids. In certain applications of the present invention, a dominating amount of polar and bilayer forming lipids may produce liposomal structures connected to protein. For example, only polar lipids in the form of phospholipids together with selected lipoproteins may form specific disc-like particles with the inventive method. If for example Apolipoprotein AI is used, these particles have considerable stability and resemble native HDL-particle structures, so the characteristics of the protein will also considerably influence the nature of the lipid particles. On the other hand, a dominating amount of nonpolar lipids (i.e. glycerides) will form lipid particles resembling emulsion droplets which are stabilized by the polar lipids (i.e. phospholipids). Also the characteristics and the amount of the protein will influence the constitution of the lipid particle and it is obvious that dependent on the physical and chemical nature of the protein and the composition of the lipid agent different types of lipid particles will result from the inventive process. It is within the ability of the skilled person to predict the particle morphology in the resultant composition from said characteristics of the main ingredients and the remaining process parameters. The skilled person will consequently be capable of designing individual lipid agents according to the general knowledge of lipid drug delivery and by means of the inventive method form lipid particles comprising a designated protein. For these reasons the general expression "lipid particle" used herein should be given a broad meaning and be regarded to include protein complexes stabilized with lipid agent which are dispersed in an aqueous solution.

Besides the requirement to withstand the shear forces from turbulent flow and cavities resulting from the high pressure homogenization of the inventive process without substantial loss of biological activity and with substantially maintained structure, the proteins must have a degree of compatibility to the lipid agent, in order to provide stable particles comprising lipid agent and protein.

In accordance with the present invention "protein" is defined as any native occurring or recombinantly or otherwise synthetically produced bioactive protein, polypeptide or oligopeptide which is capable of a sufficient hydrophobic interaction with a lipid agent as previously defined. Sufficient hydrophobic interaction will mean that the protein at least partially interacts with the lipid agent in order to form lipid particles predominantly by hydrophobic forces rather than electrostatic attraction. In the resulting products the protein can, for example, be partially embedded into the lipid particle, penetrate into the core of lipid particle, or constitute other forms lipid protein complexes. This also excludes that the protein is simply entrapped into the aqueous phase of a liposome, as is disclosed in the aforementioned Liposome Technology, 1993 by CRC Press Inc., Vol. 1, Ch. 3, pp. 49–63: M M Brandl et al. and by A L Weiner in Immunomethods, 1994, Vol. 4, pp. 201–209. Suitable proteins preferably belong to categories 2 and 3 as defined by Y-L Lo et al. on page 805, column 2 of the article in Journ. Of Pharm. Sci, 1995, Vol. 84(7), pp. 805–814. Especially suitable proteins are membrane proteins as defined on pages 274–275 in Principles of Biochemistry, $7^{th}$ Ed, E L Smith et al and lipoproteins according W V Rodrigueza et al. in Advanced Drug Delivery Reviews, 1998, Vol. 32, pp. 31–43 which frequently spontaneously interact with liposome like lipid particles to form new integrated lipid-protein particles.

According to another aspect of the present invention the protein contributed to provide the lipid particles with desired physiochemical or biological properties, such as improved stability in a dispersed system, targeting functions and functions which affect their biological distribution and elimination. In this aspect, the lipid agent may comprise a therapeutically active agent dissolved or dispersed in said lipid agent which can employ the resulting dispersed system as an improved drug delivery system. In such a case a reduction of the lipid particle size can be accomplished. At the same time the association of the protein to the surface of the lipid particle is facilitated with hydrophobic interactions as described above. This exemplified by forming a convention lipid emulsion for parenteral use with protein associated to the surface which can have certain parts embedded in the surface phospholipid monolayer or the oily core of the particle. It is understood that such an emulsion can comprise a specific therapeutic agent associated with the emulsion particles in manners well known to persons skilled in this art.

To be capable of hydrophobic interaction, it is preferred that the protein is at least partially lipophilic, i.e. has a lipophilic domain and/or is capable to interact with bilayer forming lipids. An example of such suitable proteins are those which exert their bioactive capacity, in connection with a surface of a biological membrane, i.e. membrane proteins. Such proteins are involved in enzymatic, transport, receptor and other functions associated with cellular membranes. Many such proteins therefore have domains which can associate with phospholipid membranes, as exemplified by so called integral proteins which are integrated directly into the bilayer of a lipid membrane. It is to be understood that functional analogs and fragments of such naturally occurring proteins can be employed with the present invention if they meet the requirements of sufficient hydrophobic interaction with the lipid agent.

More preferably, the protein has at least partially amphiphilic properties in a helix and a high capacity of interaction with bilayer forming lipids, as exemplified by the lipoproteins associated with lipid transport in the blood system. It can be expected that such proteins have a high number of exposed hydrophobic residues will have a favorable associated rate in forming lipid particles with the lipid agent. Examples of especially preferred protein are such membrane proteins or lipoproteins which have a hydrophobic alpha-helix part.

It is also to be understood that proteins otherwise unsuitable to be subjected to the inventive method, due to insufficient hydrophobic interaction with lipids, readily can be adapted thereto by the introducing a group to the native protein structure which is compatible with the lipid agent. A suitable group for introducing lipid compatibility by compexing or by covalent attachment can be a peptide fragment having a number of designated amino acids which contribute to the formation of suitable characteristics, for example, an amphiphilic helix as suggested in the mentioned U.S. Pat. No. 4,643,988. Also other types of groups with lipid compatible characteristics, for example having hydrophobic acyl group residues, can be associated to the native protein with covalent bonds or other types of linkages. Potentially such groups, may be complemented with targeting functions, in order to improve the direction of the drug to its active site and thus optimize its beneficial activity. The person skilled in protein chemistry will be able to find a number of such groups, suitable for designing a more lipid agent compatible protein conjugate and to design it so that the bioactivity of the protein remains substantially unaffected. Moreover, such groups can be designed to be enzymatically cleaved in-vivo in suitable manner, without contribute to adverse effects in terms of undesired accumulation of the complementary lipid compatible substances.

Examples of proteins preferred according to specific aspects of the present invention are the apolipoproteins A-I, A-II, A-IV, B, C-I, C-II, C-III, D and E or functional analogues and derivatives thereof, such as the small peptides described in the mentioned U.S. Pat. No. 4,643,988, and the like. Of these apolipoproteins, apolipoprotein AI (ApoA-I) and its natural variants such as apolipoprotein A-IM (Milano) (Apo A-IM) can be prepared by conventional separation technology from serum or with recombinant technology, disclosed in for example WO 9312143, WO 9413819 or in WO 9807751.

According to preferred embodiment of the present invention lipoproteins (particularly apolipoproteins) having an amphiphilic helix, as defined above, will be used as the protein and the lipid agent will be substantially only phospholipids. The process will then result in disc-formed or discoidal lipid particles which resemble native HDL-particles, essentially similar to those mentions in the articles above.

It is the particular aim of the inventive method to facilitate the hydrophobic interaction between the lipid agent and the protein while at the same time disperse lipid agent into particles. To accomplish that it is an important and characteristic feature of the present invention that the protein solution and the lipid agent, either premixed or separated, shall be introduced to a high pressure homogenization and be subjected to high pressure homogenization at conditions sufficient to form discrete lipid particles which comprise protein in a high yield, so substantially no, or only small amounts of free lipid agent and free protein remain. The high pressure homogenization serves to provide the components with a suitable amount of mechanical energy to increase their compatibility and capacity to interact. More specifically, the energy supplantation during the homogenization will facilitate the interaction of the hydrophobic parts of the lipid agent and the protein which otherwise might be shielded in an aqueous environment.

As previously mentioned, a homogenization station according to the present invention comprises a homogenizer, but may also include means for performing a premixing step of the protein solution and the lipid agent. In the premixing treatment, all the components are manually or automatically added and co-mixed using suitable mixer, like Ystral GmbH and similar types of conventional mixers.

For the homogenization treatment, a single homogenizer can be employed and the homogenization can be carried out by one step operation, through multi-pass operation, or by a continuous operation. Also, multiple homogenizers may be employed in a series configuration, each carrying out one homogenization pass. Many commercially available homogenizers capable of being operated at a high pressure can be used in accordance with the present invention, for example Rannie high pressure homogenizer, Avestin, Gaulin homogenizers, Microfluidizers and the like.

Vessels, suitable for the homogenization preferably are conventional, commercially available vessels for pharmaceutical manufacturing, preferably jacketed vessel of stainless steel. Temperature regulation may be achieved by commercially available temperature regulators, like Julabo ATS 2 reactor temperature regulator. To provide an inert atmosphere during the manufacturing process, preferably filtered $N_2$ gas is used.

In order to accomplish the method of preparing the lipid particles comprising protein and successfully carry out the present invention, it is of importance that the homogenizers are operated at a high pressure which exceeds about 200 bar, but is below about 2000 bar. Preferably, the homogenizer is operated at about 600 to about 1200 bar.

In the case of a continuous operation, the homogenization time is primarily determined by the lipid particle-protein yield, the homogeneity, the particle size and zeta potential, in combination with the homogenization temperature and pressure. In the case of multi-pass operation, wherein the protein and lipid agent are subjected to several cycles of homogenization, i.e. several passages, it is rather the number of homogenization passes which is optimized instead of homogenization time. Generally, the skilled person realize that a homogenization according to the present invention requires an adaptation of pressure, process time and temperature for each individual system of protein of lipids in order to achieve desirable result in terms of yield and process efficacy, as well as maintained protein activity.

In accordance with the inventive processes, volume of the batches can be varied from small scale production in the range of 1 ml to 5 l, while up to about 20,000 l is easily achieved for normal large scale production.

In order to comply with such a potentially detrimental influence from the single high pressure homogenization, it is within the scope of the present invention to introduce plural cycles of homogenization at gentler, somewhat lower pressure and allow for one or several intermediate rest periods in-between. The skilled person will have no difficulties to design individual running operations for specifically sensitive proteins and thereby be able to apply the inventive process for a large number of compositions to form lipid particles comprising protein.

An additional, important aspect of the present invention is the possibility to obtain improved aseptic conditions with the inventive method, since many microorganisms will not withstand high pressure homogenization. According to one embodiment of the present invention, the homogenization therefore can be performed in at least two sequences with an intermediate incubation period. The use of repeated cycles of high pressure homogenization with intermediate resting or incubation periods successively can reduce the amount of viable microorganisms in the final formulation of lipid particles, without introducing any other form of sterilization measures, such as heat or irradiation which risk to destroy the protein or adding such complementary preservative agents which may lead to problems with the tolerability of the product.

Another aspect of the present invention is to allow for an incubation step during a certain, suitable time period subsequent to the homogenization procedure, but before the collection of the resulting lipid particles for optional further processing into a pharmaceutical product. The reason being that there is tendency that the yield can increase during such a period.

As mentioned, the formulation and the process parameters must be optimized with respect to each chosen composition of protein and lipid agent. It is of high importance to consider the phase behavior, especially at different temperatures, of both the protein and the components of the lipid agent. Moreover, the capacity of the protein to withstand without being impaired in structure and/or activity of the high shear forces resulting from the high pressure homogenization must be carefully considered. Local development of heat during the treatment must also be considered, since temperatures in the homogenization process in range of 10 to 95° C. normally are encountered.

Moreover, the process parameters of the homogenization treatment, principally pressure, temperature, running time, number of homogenization cycles and incubation and the like, also will affect the lipid particle size, its size distribution and the yield of complexed lipid agent and protein. For example, it might generally be expected that the yield will increase with more homogenization cycles, but the skilled person should be able to compromise between this advantage and other aspects resulting from the homogenization treatment.

According to the particular embodiment of the present invention when the lipid agent essentially consists of a phospholipid, it is preferred to operate at a temperature close to, or above, the phase transition temperature (Tc), at which the phospholipid is transferred from gel form into liquid crystalline form. The characteristics of the protein will also influence the efficacy of lipid particle formation, since a higher number of hydrophobic exposed residues of the protein will lead to a higher association rate with the phospholipid, whereas lower molecular weight of protein also will increase the rate of forming stable particles. Therefore, for the case when the protein is an apolipoprotein, it is predictable that the association rate is faster near the transition temperature of the phospholipid. In the case where the phospholipids are selected among phospholipids of saturated fatty acids only, it is preferred that the temperature during the homogenization is above about 42° C. for a dipalmitoyl phosphatidyl choline and above about 24–25° C. for dimyristoyl phosphatidyl choline.

According to a first specific embodiment of the present invention the lipid agent essentially comprises phospholipids and the protein has amphiphilic properties, such as lipoproteins. An important aspect of this embodiment is to enable a protection of the amphiphilic protein by the lipid agent and provide it with improved functional characteristics including stability during preparation, purification, handling and storage and the introduction of specific biological properties, such as modulation of uptake and distribution in the body, activity, degradation rate and the like. In certain applications, it is often sufficient to employ relatively rather small amounts of lipid agent which serve to protectingly interact with local hydrophobic domains of the protein. On the other hand, certain proteins require an interaction with membrane like lipid complexes to be stabilized and/or acquire a desired bioactivity (obtain a proper orientation in lipid bilayer structures) which means that a relatively higher amount of lipid agent must be added according to the inventive methods, Preferably the phospholipids of this embodiment of the invention essentially comprises phosphatidyl cholines separated from phospholipids of native origin, such as soybean or egg yolk phospholipids or is synthetic or semi-synthetic phosphatidyl cholines with controlled content of acyl groups. Most preferred are soybean derived phosphatidyl choline, dipalmitoyl phosphatidyl choline and dimyristoyl phosphatidyl choline. The protein preferably is a human lipoproteins, such as an apolipoprotein and the lipid particles resulting from the inventive method will find use in therapeutic or prophylactic treatment of diseases connected to lipids or lipoidal substances, including the lowering of amounts of cholesterol and endotoxins. Most preferred apolipoproteins are apolipoproteins A or E including their natural or synthetic variants, such as recombinantly produced mutant apolipoprotein A-I$_{Milano}$. The phospholipids preferably are added to an aqueous protein solution in a premixing step in weight relationship of lipid to protein of from about 1:100 to about 10:1 (w/w). As a reference to the lower limit of lipid to protein ratio, it is referred to albumin in its native fatty acid transporting function where the lipid to protein ratio is about 1:100 (w/w). Preferably, the amount of lipid agent to protein in accordance with this embodiment of the present invention is from about 1:4 to about 4:1 and more preferably between about 1:1 to about 3:1. Generally, it is aimed to obtain a yield of lipid-protein complex over 90% and preferably close to 100%, so little or almost no non-associated protein or lipid agent is obtained in the resulting lipid particle composition. It is also highly desirable to have as low amounts of phospholipids as possible in any injectible preparation, since excessive amounts may produce bilayered vesicles (e.g. liposomes) which conceivably might induce side effects in the subject receiving such a preparation. The high pressure homogenization is performed during a suitable time and temperature at a suitable pressure in the range from about 200 bar to about 1500 bar, preferably from about 600 to about 1200 bar and. The homogenization can be performed in one or several periods with an intermediate rest period of a suitable duration with an optional subsequent incubation step. This method results in a high yield from about 90 to 100% of discoidal lipid particles comprised of phospholipids and protein with a particle size ranging from about 7 to about 25 nm. The protein incorporated in the lipid particles formed by the inventive method has maintained its chemical identity in terms of oxidation and deamidation. The lipid particles therefore will be capable of exerting the same biological activity as protein not subjected to homogenization when incorporated in a final pharmaceutical preparation.

According to a second specific embodiment of the invention, the solution of an amphiphilic protein is contacted with an aqueous lipid dispersion, preferably an oil-in-water emulsion (lipid emulsion) in a method including high pressure homogenization. The lipid dispersion preferably is a conventional emulsion for parenteral use which have clinical acceptance, such as Intralipid, Liposyn or other emulsions based on a triglyceride oil of vegetable origin (soybean, safflower oils) and a clinically acceptable emulsifier, such as egg yolk or soybean phospholipids. The skilled person will be able to vary the contents and composition of the emulsion, for example in accordance with discussion of suitable nonpolar lipids above. It is preferred that the emulsion comprises about 1 to 50% (w/w) of an oil phase and about 0.05 to 30% (w/w) of a phospholipid emulsifier and that the oil phase comprises triglyceride oils (triglycerides preferably of long chain saturated or unsaturated fatty acid and/or medium chain fatty acids) or alkyl esters of fatty acids suitable for parenteral administration. Person skilled in emulsion technology will readily find suitable lipid emulsions which are applicable in the inventive method. The relationship between lipid agent (nonpolar lipid and emulsifier) and protein typically may vary between about 500:1 to about 10:1 (w/w) and preferably between about 60:1 and 20:1. However, the skilled person will be able deviate from these recommendations in certain applications required by the characteristics of the lipid agent and the protein and the specific clinical utility of the product. For example, it can be desirable to retain a high nutritional value of the lipid particle composition or to comprise a high amount of a lipid in order to be able to incorporate a lipid soluble additional therapeutic agent in the lipid particles. Alternatively the lipids have a therapeutic and diagnostic value per se, for example as carriers of beneficial fatty acids or diagnostic value or as contrast agents having for example iodinated fatty acids for delivery to a target organ. In such applications, the inventive method is useful for linking proteins to the lipids and thereby modify the distribution and elimination of the resulting lipid particles. The inventive method can according to this aspect be used to obtain a protein coating of the lipid particles which contains a relatively low amount of protein compared to lipid. Such a coating of the lipid particle can result in a modified interaction with the natural recognition of the immune system as accomplished by linking antibodies to the lipids with the inventive method. In such a case, the ratio lipid to protein can be extremely high, since it is conceivable that as few as less than thousand protein molecules are sufficient to associate to the outer region of the lipid particle and yet obtain significant results. On the other hand, the proteins can also be employed to change the chemical physical characteristics of the dispersed lipid particles by using the inventive method. For this case a higher protein load can be required resulting a smaller lipid to protein ratio. The high pressure homogenization of lipid emulsion and protein is performed during a suitable time and at suitable temperature at a high pressure preferably not exceeding about 2000 bar, more preferably being in the range from about 200 bar to about 1500 bar and most preferably from about 600 to about 1200 bar. The protein is preferably is an apolipoprotein which will find use in therapeutic of prophylactic treatment of diseases connected to lipids or lipoidal substances, including lowering of amounts of cholesterol and endotoxins. Most preferred apolipoproteins consists apolipoproteins A or E including their natural or synthetic variants, such as recombinantly produced mutant apolipoprotein A-I$_{Milano}$. The lipid particles resulting from the homogenization with an emulsion preferably have a mean particle size less than about 1 µm and preferably in the range of about 0.1 to 0.5 µm. The lipid particles with associated protein will to different extents have a modified zeta potential in comparison to the lipid particles of the original emulsion which may provide the resulting preparation with an improved physical stability which also is an indication that the amphiphilic protein (at least partially) is associated with the surface layer of the lipid particles. Generally, a non-favorable zeta potential should be avoided due to risks of aggregation of lipid particles which might inflict embolism after intravenous administration. It is therefore often necessary to induce a contribution to the net charge of the resulting lipid particles. This can be accomplished by conventional measures, such as a pH change, introduction of a supplementary stabilizing charged agent and the like.

After the homogenization step of the inventive methods is completed referred to above is completed, the lipid particles of each batch are collected with conventional measures and equipment, which may include centrifugation or filtration to improve the concentration and the purification of the lipid particle product, as well as conventional processing to obtain an aseptic product.

The so formed product can the be subjected to conventional lyophilization optionally with the addition of suitable excipients, so as to form a final pharmaceutical solid product, suitable for long-term storage and subsequent reconstitution with an aqueous fluid, just prior to its parenteral administration, for example by intravenous injection. Reconstitution may be accomplished by addition of buffer solution containing suitable excipients with respect to tonicity as well as rate of dissolution. Suitable buffer includes sodium phosphate, histidine and the like. Excipients include polyols, like mannitol, glycerol, saccharose and amino acids.

According to an embodiment of the present invention the lyophilization, can be performed batch-wise, in-situ, in designated chambers of conventional multi-chamber cartridges, or alternatively directly in a chamber located in the barrel of a multi-chamber injection device. These devices will form kit-of-parts comprising the one or plural dosages of solid composition in a chamber separated from a neighboring chamber, storing an aqueous parenterally administerable reconstitution fluid, by means of a movable wall which can be displaced in order to form an injectible fluid, just before the desired administration. The skilled person can readily find several examples of such syringes or cartridges which can be operated by pen type syringe devices (see e.g. EP 298 067).

Examplifying Description of the Invention

EXAMPLE 1

0.687 g SPC (soy bean phosphatidyl choline) is mixed in a premixing step in a jacketed vessel with 45.80 g of a protein solution comprising apolipoprotein A-$I_{Milano}$,(Apo A-IM) obtained from the downstream process from recombinant production with a protein concentration of 12 mg/ml, in sodium phosphate buffer. The ratio lipid to protein was thus 1.25:1. The temperature was regulated to 60° C. by a Julabo ATS 2 reactor temperature regulator. An Ystral mixer in a rotor and stator configuration is used as mixer with stirring speed controlled at 2000 rpm. After 10 minutes of pre-mixing, the mixture is homogenized in a mini Rannie homogenizer, Mini-Lab type 7.30 VH, at a pressure of 1000 bar, 60° C. continuously for 5 minutes. This method results in the formation of transparent solution of lipid-protein particles with a structure resembling disc-formed native HDL-like complex. The yield of protein incorporated into lipid complexes as detected by native-PAGE is 98% (according to the method described below) In a replicate experiment the yield was 100%, demonstrating the reproducibility of the process.

EXAMPLE 2

0.47 g of recombinant apolipoprotein A-$I_{Milano}$,(Apo A-IM), (9.6 mg protein/ml in a phosphate buffer) and soybean phosphatidyl choline (SPC) added to 1:1 lipid/protein ratio (w/w) was premixed at 60° C. for 10 minutes and then homogenized for 5 minutes at 60° C. and 1000 bar in the mini-Rannie homogenizer of Example 1. All protein was incorporated into 8 nm lipid-protein particles as measured by n-PAGE (according to the method described below). Accordingly, it is demonstrated that a high incorporation of apolipoprotein A-$I_{Milano}$ into lipid-protein particles is obtained in the homogenization process although a low ratio of lipid to protein is used.

Figure 1:
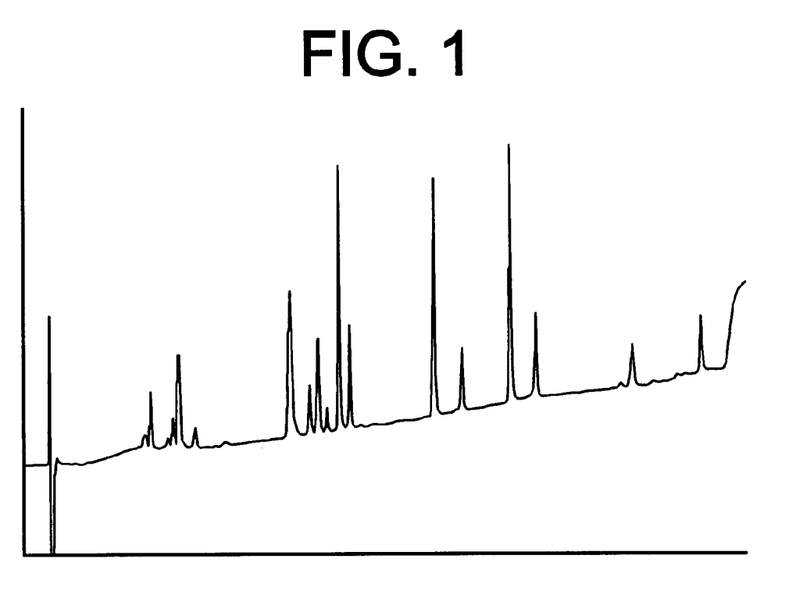
FIG. 1 demonstrates peptide maps of the mutant apolipoprotein A-$I_{Milano}$, before homogenization together with phospholipids.
Figure 2:
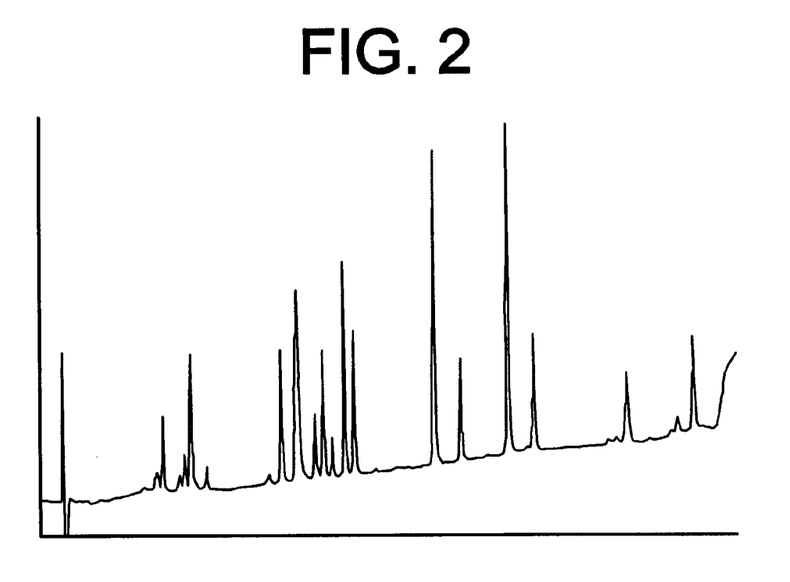
FIG. 2 demonstrates a peptide map of the mutant apolipoprotein A-$I_{Milano}$ after high pressure homogenization with phospholipids.

A similar experiment was performed with same components and during the same conditions as above, except that the homogenization was performed at 560 bars for 7 minutes at 60° C. According to subsequently performed chromatographic and electrophoretic analyses, the protein is essentially unchanged in the process. This is exemplified in FIG. 1 and FIG. 2, revealing data from peptide mapping (according to the method described below) of the apolipoprotein A-$I_{Milano}$ and the same protein after homogenization with lipid to form protein-lipid complexes.

EXAMPLE 3

Figure 3:
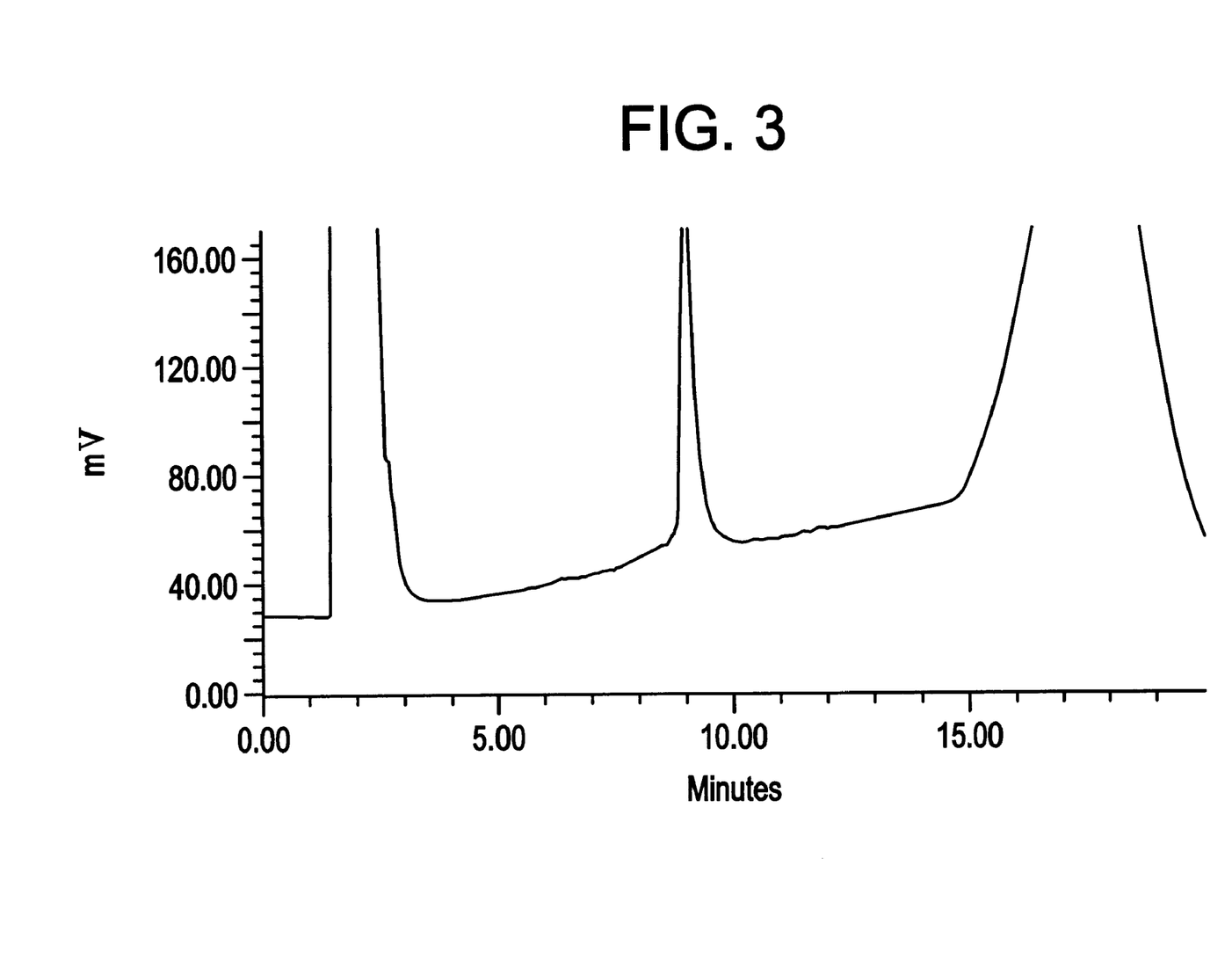
FIG. 3 demonstrates a reverse phase chromatogram (HyTach) of the reduced mutant apolipoprotein A-$I_{Milano}$, before homogenization together with phospholipids.
Figure 4:
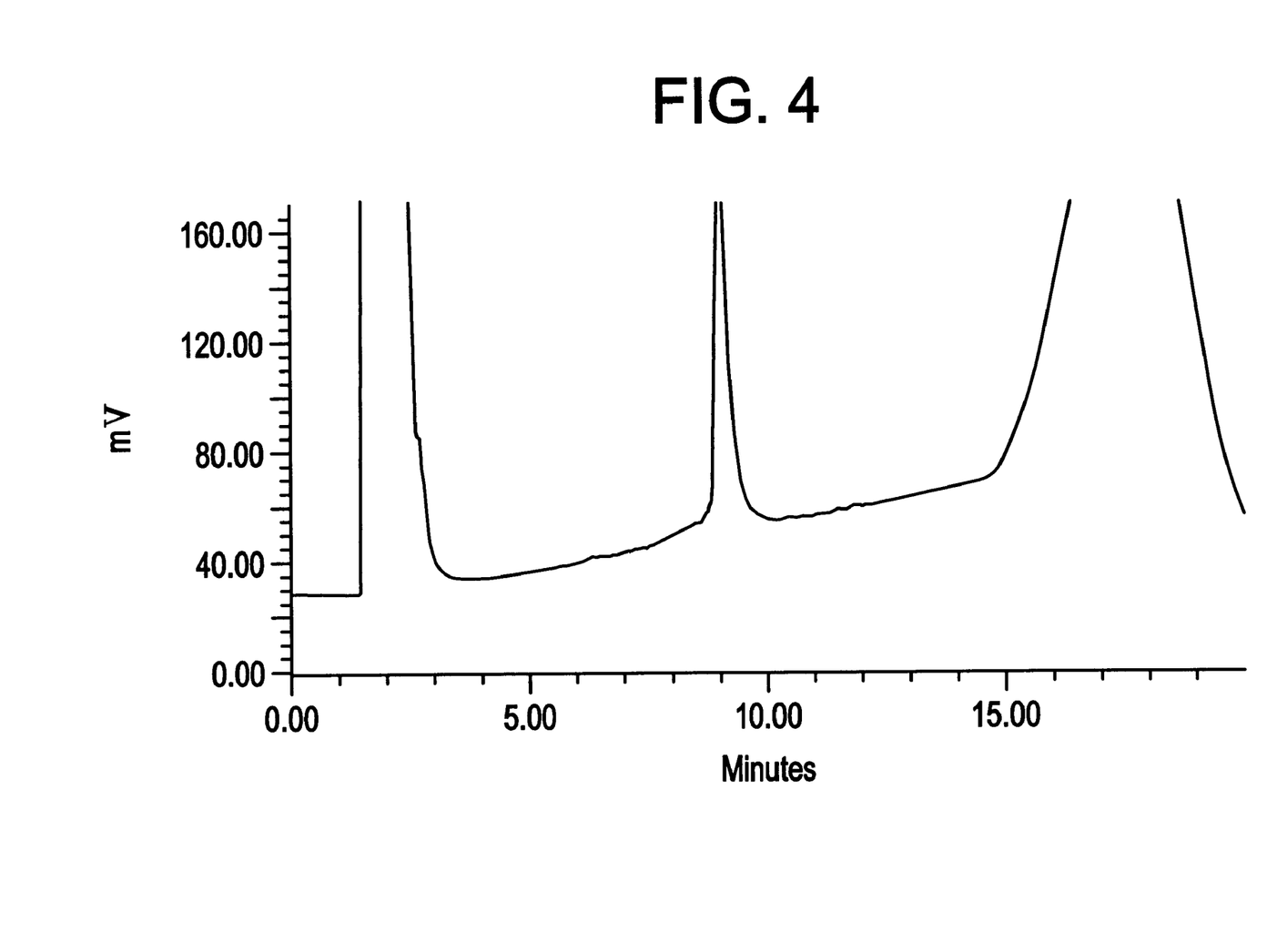
FIG. 4 demonstrates a reverse phase chromatogram (HyTach) of the reduced mutant apolipoprotein A-$I_{Milano}$ after high pressure homogenization with DPPC.

69.00 g of a solution of recombinantly produced Apo A-IM (19.8 mg/ml solution in water) was homogenized together with 4.485 g dipalmitoyl phosphatidyl choline (DPPC) at 42° C. and 1000 bar for 60 minutes with a Mini Rannie homogenizer. Before homogenization, the mixture was pre-mixed for 5 minutes at 42° C. at 2000 rpm in a nitrogen atmosphere. The ratio DPPC: Apo A-IM was 3.3:1 (w/w). Analysis for protein denaturation (deamidation, oxidation or aggregation) was made by peptide mapping, isoelectric focusing, size exclusion chromatography and reverse phase chromatography (HyTach). The data for the Apo A-IM protein in the processed material was in compliance with protein material which was not subjected to homogenization, as demonstrated by HyTach data in FIG. 3 and FIG. 4 (measured with a method disclosed below). The amount of protein incorporated into lipoprotein particles (in the size range 7.7–15.7 nm) was 100% according to densitometric scans of n-PAGE stained gels (see below). The corresponding hydrodynamic radius of the reference protein was estimated to 7.3 nm. To confirm that the particles contained phospholipid as well, the n-PAGE gels were also stained for lipids. This example demonstrates the efficient formation of lipid-protein complexes at a different composition and process condition, and the fact that the protein is essentially unaffected by the mechanical treatment together with lipid.

EXAMPLE 4

75 g of a solution of recombinantly produced Apo A-IM, 15 mg/ml with dipalmitoyl phosphatidyl choline (DPPC) added at a ratio of 2.9:1 (w/w) in 10 mM sodium phosphate (pH=7.5) was homogenized after a 5 minute pre-mixing step under the same conditions as in Example 3. The homogenization was performed with a first homogenization period of 7.5 minutes at 60° C. and 1000 bar followed by a second homogenizing period of 5 minutes at 40° C. and 1000 bar. After the first homogenizing period the amount of protein incorporated in lipid-protein particles of 7.7 to 25 nm was 78% which increased to 94% after the second homogenizing period.

There were no aggregation, truncation, deamidation or oxidation observed by chromatographic or electrophoretic methods in the proteins subjected to the two-step homogenization process.

EXAMPLE 5

Figure 5:
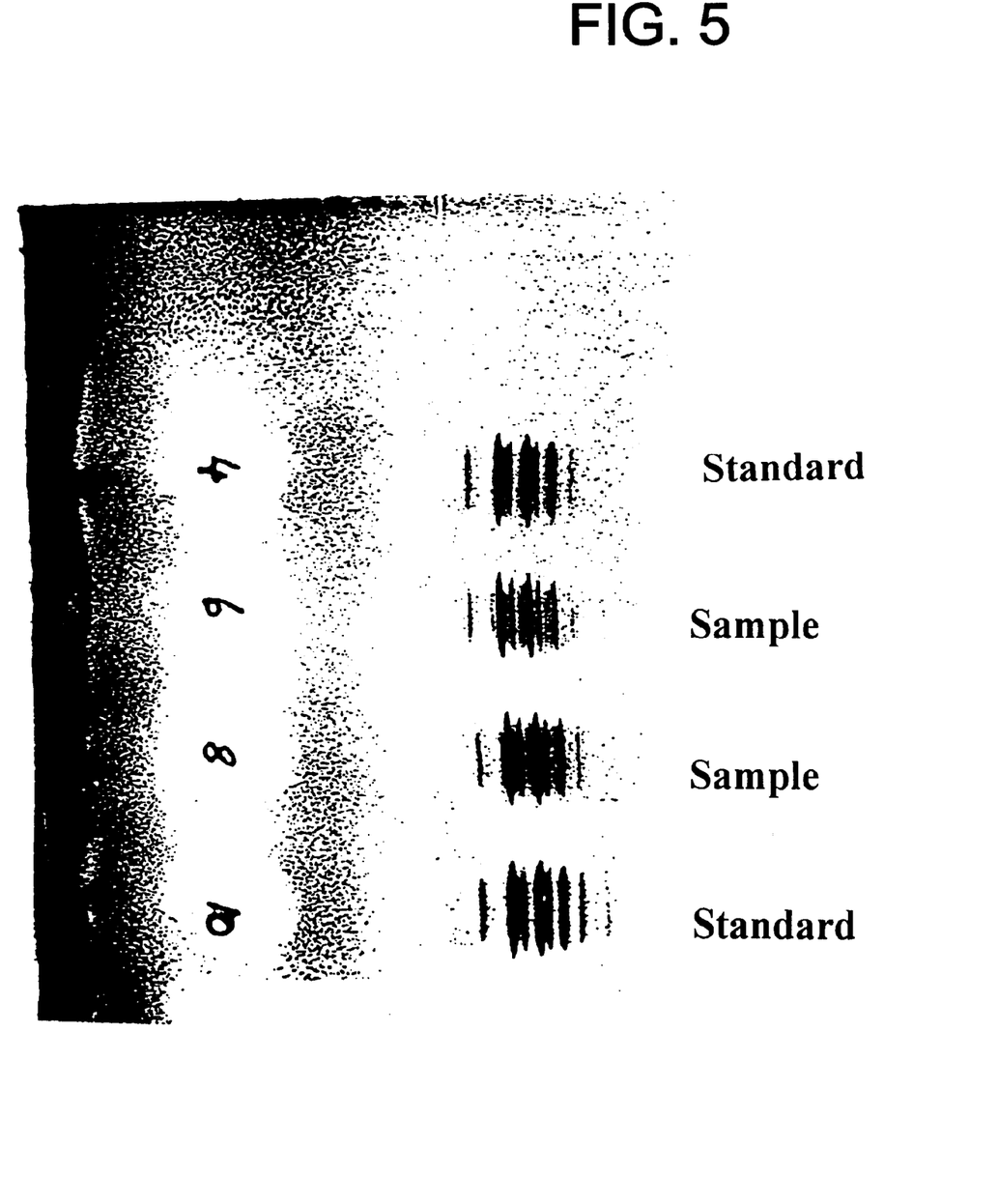
FIG. 5 shows an IEF-diagram comparing apolipoprotein A-$I_{Milano}$ treated with lipid and homogenized according to the present invention in comparison to the same, untreated protein.

263 g of dipalmitoyl phosphatidyl choline (DPPC) was added to 6.7 kg of a solution of recombinantly produced Apo A-IM, 13 mg/ml, in 10 mM sodium phosphate (pH 7.5). The material was pre-mixed for 10 minutes at 50° C. with an Ystral X 20 D-mix equipment. The material was thereafter homogenized at 42° C. and 900 bar in a high pressure homogenization of the type Lab. Rannie 12.51-H. The homogenization was performed for 35 passages where each passage has duration of 3 minutes. After the homogenization 243 g sackaros and 31 g mannitol were added and dissolved, whereupon the solution was sterile filtered, aseptically filled and freeze-dried. Subsequent electrophoretic and chromatographic analyzes of the product after its reconstitution showed that the protein was in compliance with the protein material not subjected to homogenization. This is demonstrated with the IEF data (FIG. 5) of a sample of the homogenized, final protein preparation according to this example in comparison to an untreated protein (according to a method disclosed below). The efficacy of the process is shown by n-PAGE tests where 99% of the protein was incorporated into lipoprotein particles in the size range 7.7 to 25 nm. This example demonstrates that high quality protein-lipid complexes can be produced in an efficient process with a comparatively low lipid/protein ratio in a scaled up process.

EXAMPLE 6

0.72 g of dimyristoyl phosphatidyl choline (DMPC) was added to 48.10 g solution of recombinantly produced Apo A-IM, in an Ystral mixer, giving a lipid:protein ratio of 1:1. Pre-mixing was performed for 3 minutes at 60° C. and 2000 rpm under nitrogen atmosphere before a homogenization for 7 minutes at the same temperature at 560 bar in a Rannie homogenizer. The so prepared lipid-protein particles were cooled to less than 30° C. The equivalent hydrodynamic radius of the discoidal complexes was determined to 15.1 nm (z average), by Malvern 4700 dynamic light scattering equipment.

Analysis of the protein-lipid complex according to the invention by reverse phase chromatography of the reduced protein (HyTach analysis) verifies the maintained integrity of the protein in the described process. Thus the level of oxidized protein is below the level of quantification for the method (0–3%), whereas the total level of modified protein is 12% compared to 8% in a reference sample of the protein.

EXAMPLE 7

This example comprises the preparation of an emulsion formulation of soybean oil in water, with the protein r-ApoA-1M using a high shear device. The formulation is compared to a reference emulsion made without added protein and also with an emulsion incubated with the same protein.

Preparation

A test emulsion (20% soybean oil and 1.2% egg phospholipids) containing r-ApoA-IM and a corresponding reference emulsion without protein was prepared in two steps. First a concentrated coarse emulsion was made by dispersing 60 g of soybean oil and 3.6 g of purified egg phospholipids in 113 g of distilled water, followed by coarse homogenization in a Rannie homogenizer (type 7.30 VH) at 60° C., with a small addition of a 1 N NaOH solution. The coarse emulsion was divided into two parts, one of which was kept at 60 ° C. To the other part (92.7 g) was added 62.1 g of distilled water and the emulsion was homogenized at 800 bars of pressure in the same Rannie homogenizer for 6 minutes at 60°. The resulting reference emulsion (A), was cooled to room temperature and dispensed on 20 ml vials.

The first part of the coarse emulsion above, was reintroduced to the homogenizer, and 62.2 g of a solution of r-ApoA-IM in distilled water (22.5 mg per ml) was added. The emulsion was homogenized at 800 bars of pressure in the Rannie homogenizer for 6 minutes at 60°. The resulting test emulsion (B), was cooled to room temperature and dispensed of 20 ml vials.

In a similar incubation experiment, an incubation sample (preparation C) of Intralipid 20% and r-ApoA-1M was prepared by gentle mixing of 8 g of Intralipid 20% with 2 g of the r-ApoA-1M solution above (containing 22.5 mg of r-Apo-A-1M per ml), at room temperature. A reference preparation (D) was prepared in a similar way, using distilled water instead of the protein solution.

Evaluation

The preparations A, B and C were immediately evaluated with respect to mean particle size and particle charge, using a MALVERN Zeta Sizer 4, with the samples diluted in a 2 mM TAPS buffer pH 8.4. The B preparation was also evaluated after 60 hours storage of the preparations at 55° C. (B, incubated). The C and D preparations were stored at 25° C. for 20 hours and at 55° C. for an additional 60 hours. Separate vials of preparation A and B were evaluated for shake stability by shaking for 66 hours at room temperature.

Results

Figure 6:
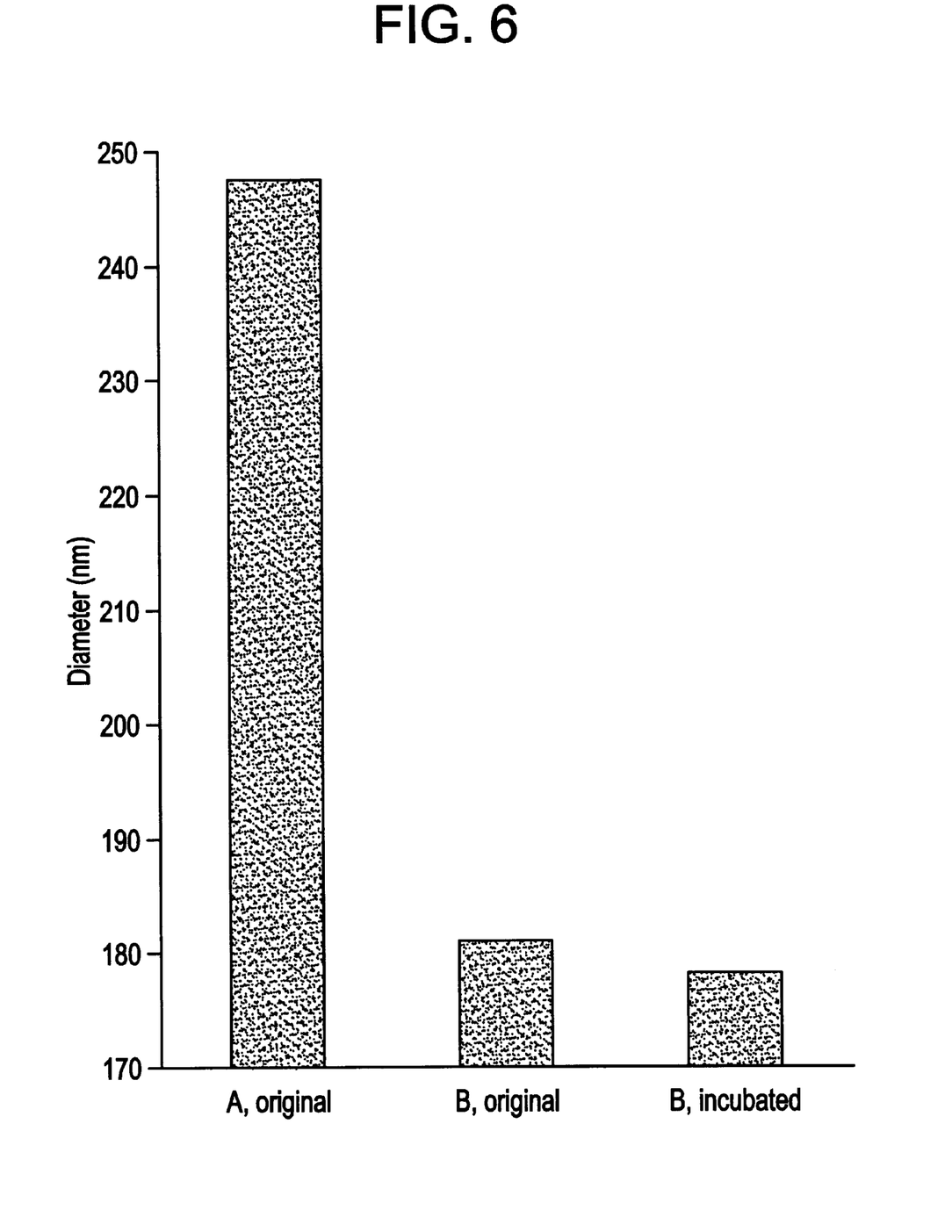
FIG. 6 shows zeta potential of a 20% soybean emulsion comprising apolipoprotein A-$I_{milano}$ when compared to references.
Figure 7:
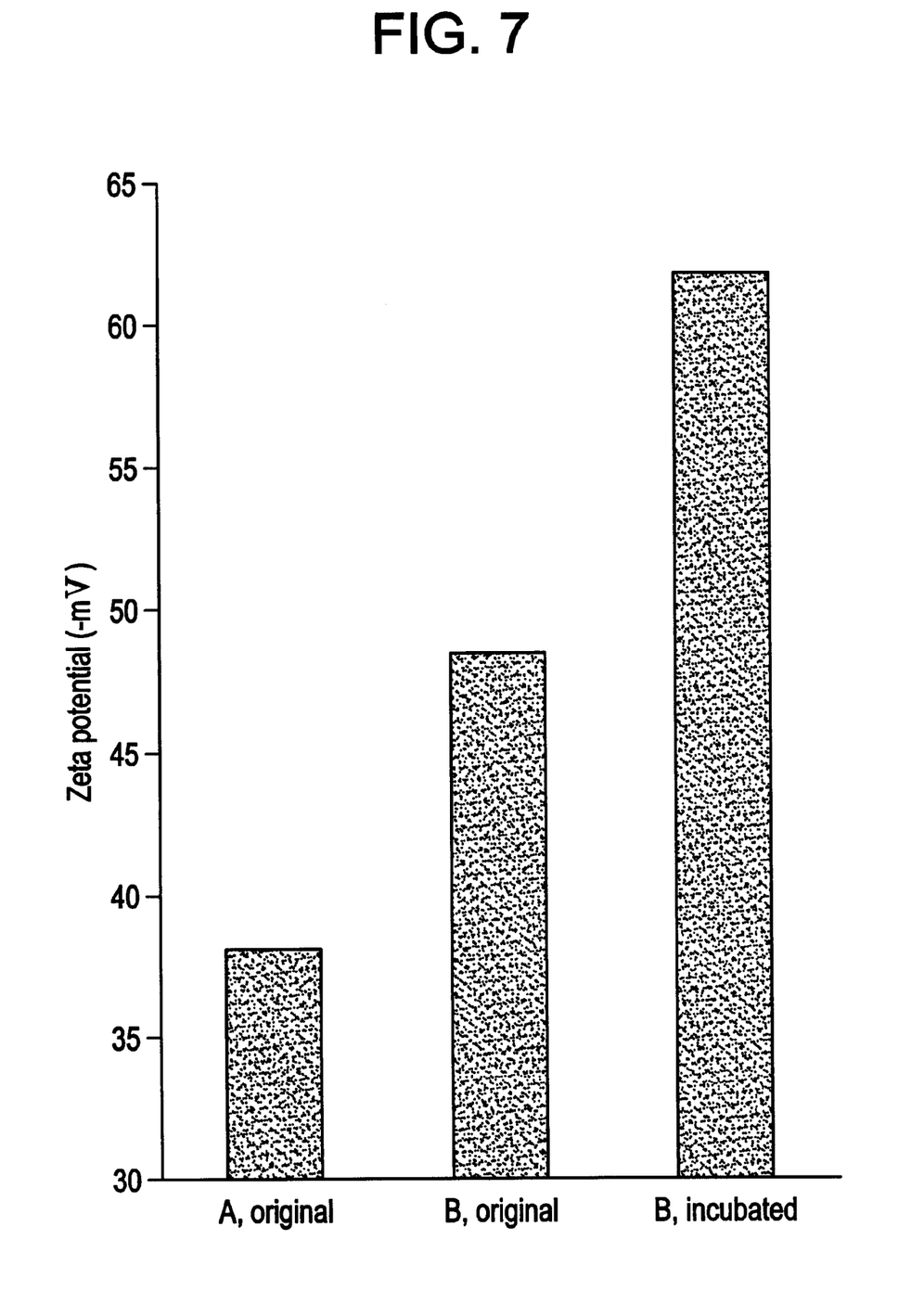
FIG. 7 shows zeta particle sizes of a incubated mixture comprising a 20% soybean emulsion and apolipoprotein A-$I_{Milano}$. when compared to references.

The results are demonstrated in FIG. 6 (particle sizes) and FIG. 7 (particle surface charge) for the emulsions in Preparations A, B, before and after incubation (B).

For preparation C and D, there is no change in particle size during the incubation period. During the incubation period the particle charge in preparation C increases by 8 mV compared to 4 mV for the reference (D). There is thus a clear indication of absorption of r-ApoA-1M to the emulsion particles during incubation. However, the absorption process is very slow and requires elevated temperatures.

Preparation B, shows a remarkably reduction in particle size (180.9 nm) compared to A, the reference preparation (247.5 nm), and the size does not change during the subsequent incubation step. Similarly there is a large difference in emulsion particle charge at homogenization (48.5 mV for test preparation B compared to 38.1 mV for preparation A), and the charge continues to increase to 61.7 mV during the subsequent incubation step.

These data indicate that recombinantly produced ApoA-IM adsorbs to, and interact with the emulsion particles to a high extent during homogenization. This influences not only the charge of the emulsion droplets but the protein also acts a an emulsifier, which enables the emulsion droplets to assume a higher surface curvature, which leads to a smaller mean particle size. During the subsequent incubation at 55° C., the continued increase in particle charge indicates a continued adsorption of protein to the surface of the emulsion particles. In the experiment where the protein is incubated with a similar emulsion, the interaction is quite different, in the sense that the particle size is essentially unchanged during the extended incubation period, and the particle charge changes to a much smaller extent during incubation.

A further indication of a high adsorption of protein to the emulsion droplets in preparation B is given by the shaking test of the preparation A and B. After the shaking period (66 hours) the preparation A demonstrated a large oil droplet on the surface of the emulsion, and also large quantities of oil on the glass surface, whereas preparation B had essentially no visible oil. This difference is explained by the stabilization of the protein-containing emulsion due to the higher charge (as indicated above) on the emulsion droplets.

These experiments demonstrate that efficient association of a partially hydrophobic protein to emulsion particles can be accomplished when the interaction between the components is facilitated by the use of a high shear device and also followed by an incubation period.

Analytical evaluation procedures

The size distribution and relative amount of the formulated recombinant lipoprotein A-IM/phospholipid were estimated by densitometric evaluation after separation by non-denaturating polyacrylamide gradient gel electrophoresis (n-PAGE) on Novex gels with a 4–20% linear gradient of acrylamide. The separation is based on size and the size distribution is estimated by comparing the samples with globular proteins with known Stoke's diameters, run on each gel. After electrophoresis the protein moieties are visualized by staining with Coomassie Brilliant Blue. The stained gels are scanned on a densitometer whereupon the gel images are processed and evaluated by the ImageMaster software. Apparent sizes and relative amounts of the protein stained bands are calculated.

Peptide mapping for identity testing of apolipoprotein A-IM was performed with a fragmentation with endoproteinase Lys-C digestion enzyme and analysis by reversed phase HPLC using a 2.1 mm i.d. Zorbax SB-C8 column. The peptide fragments are separated and detection is performed with UV detection at 220 nm. The sample peptide is compared with standard material digest. Oxidized forms, truncated forms and unknown new peaks are observed with this method. This separation technique is based on reversed phase chromatography at pH 2 with a step gradient from 3% acetonitrile to about 38%. A Zorbax Staplebound columns with 2.1 mm inner diameter was used with flow rate of 0.21 mm during a 90 minute analysis.

Quantitative determination and purity of recombinant apolipoprotein A-IM was performed with reversed phase HPLC utilizing a HyTach column. This method aims to differentiate between i) the monomer form of recombinant apolipoprotein A-IM (r-ApoA-IM) and modified monomeric forms of the protein and ii) the intact dimer form and modified dimeric forms of the protein. The differentiation between intact and modified forms of the protein is made possible by first reducing the protein with mercaptoethanol to ensure that dimeric forms not are present. The impurity content of the r-ApoA-IM samples are expressed as the area percentage of changed monomeric forms including unknown peaks of the total peak area seen in the gradient interval. To differentiate between intact r-ApoA-IM dimer and dimeric variants, the reduction procedure is omitted. The dimeric forms are separated from the monomeric ones, thus all of the present r-ApoA-IM forms are determined in the analysis. The separation technique, reversed phase chromatography, mainly separates according to hydrophobic differences of the molecule. This is useful for the separation of truncated forms and degraded forms from intact protein, due to differences in hydrophobicity. Quantitation of the intact r-ApoA-IM monomer (after reduction of the protein) is determined on the peak corresponding to intact monomer only. The concentration is determined by constructing a calibration graph with r-ApoA-IM reference material at four levels. The separation is performed with 2 μm non-porous C18 modified silica particles. The mobile phase consists of 0.25% trifluoroacetic acid in water-isopropanol mixture. The protein is eluated in a gradient run with increasing organ solvent from 52 to 62%.

The IEF analysis of r-ApoA-IM was performed on the gel Immobiline DryPlate 4–7, a polyacrylamide gel with an immobilized linear pH gradient. The proteins are electrophoretically separated in the pH gradient according to their isoelectric points (pI), i.e. when the net charge within the molecule is zero.

What is claimed is:

1. A method of preparing a composition of lipid particles comprising a lipid agent and a protein, wherein said protein is an apolipoprotein, in hydrophobic interaction comprising:
    (i) introducing a protein preparation and a lipid agent, the protein capable of hydrophobic interaction with the lipid agent, to a homogenization station;
    (ii) subjecting resulting fluid mixture of protein and lipid agent to high pressure homogenization at a pressure from about 200 bar to about 2000 bar; and
    (iii) collecting the so formed composition of lipid particles, thereby yielding at least 75 percent lipid associated protein.

2. The method according to claim 1 comprising mixing the protein preparation and the lipid agent to a homogenous fluid mixture before the homogenization.

3. The method according to claim 1 wherein the protein preparation is an aqueous solution of the protein.

4. The method according to claim 1 wherein the high pressure homogenization is performed at a pressure of at least about 200 bar, but not exceeding about 2000 bar.

5. The method according to claim 4 wherein the high pressure homogenization is performed at a pressure of about 600 to about 1200 bar.

6. The method according to claim 1 wherein the homogenization is performed in at least two sequences with an intermediate incubation period.

7. The method according to claim 1 wherein the yield is 90 percent lipid associated protein.

8. The method according to claim 1 wherein the lipid agent is at least partially in a solid form providing a dispersion with the protein preparation before the homogenization.

9. The method according to a claim 1 wherein the lipid agent comprises amphiphilic compounds.

10. The method according to claim 9 wherein the lipid agent comprises phospholipids.

11. The method according to claim 10 wherein the phospholipids comprise phosphatidyl choline of natural or synthetic origin with a defined fatty acid composition.

12. The method according to claim 11 wherein the phosphatidyl choline is selected from the group consisting of egg yolk choline, soybean phosphatidyl choline and phosphatidyl choline having acyl groups of fatty acids with between 14 and 18 carbon atoms.

13. The method according to claim 12 wherein the phosphatidyl choline is dipalmitoyl phosphatidyl choline.

14. The method according to claim 9 wherein the lipid agent further comprises at least one nonpolar lipid.

15. The method according to claim 14 where the nonpolar lipid is selected from the group consisting of glycerylesters, alkylesters, cholesterol and nonpolar derivatives of cholesteral.

16. The method according to claim 1 wherein the amount of lipid agent in relation to protein is about 1:100 to about 10:1 (w/w).

17. The method according to claim 16 wherein the amount of lipid agent in relation protein is about 1:4 to about 4:1.

18. The method according to claim 1 wherein the lipid agent is a dispersion of lipids in an aqueous medium.

19. The method according to claim 18 wherein the dispersion of lipids is an oil-in water imulsion.

20. The method according to claim 19 wherein the emulsion comprises about 1 to 50% (w/w) of an oil phase and about 0.5 to 10% (w/w) of a phospholipid emulsifier.

21. The method according to claim 20 wherein the oil phase comprises triglyceride oils or alkyl esters of fatty acids suitable for parenteral administration.

22. The method according to claim 19 wherein the lipid particles have a mean particle size less than about 1 µm.

23. The method according to claim 22 wherein the lipid particles have a mean particle size range of about 0.1 to about 0.5 µm.

24. The method according to claim 18 wherein the amount of lipid agent in relation to protein is about 500:1 to about 10:1 (w/w).

25. The method according to claim 18 wherein a therapeutically active agent is dissolved or dispersed in the lipid particles.

26. The method according to claim 1 wherein an additional agent selected from a group consisting of polyols, mono-, di- and polysaccharides and amino acids is added to the mixture of protein and lipid.

27. The method according claim 1 wherein the protein is capable of hydrophobic interaction with the lipid agent.

28. The method according to claim 27 wherein the protein is at least partially lipophilic.

29. The method according to claim 28 wherein the protein is a membrane protein, a lipoprotein, or an active fragment thereof.

30. The method according to claim 27 wherein the protein has an alpha-helix domain capable of hydrophobic interaction with the lipid agent.

31. The method according to claim 1 wherein the protein is bioactive and capable of being subjected to shear force associated with homogenization at a pressure from about 200 bar to about 2000 bar without substantial loss of its biological activity.

32. The method according to claim 1 wherein the protein exerts a stabilizing influence on the resulting lipid particles.

33. The method according to claim 1 wherein the protein is selected from the group of apolipoproteins consisting of apolipoprotein A, apolipoprotein E, natural variants of apolipoprotein A, natural variants of apolipoprotein E, synthetic variants of apolipoprotein A, and synthetic variants of apolipoprotein E.

34. A method of preparing a composition of lipid particles according to claim 1 comprising purifying and concentrating the composition of lipid particles to a pharmaceutically acceptable composition.

35. The method according to claim 1 comprising lyophilizing the composition of lipid particles to a final pharmaceutical product.

36. A composition of lipid and a bioactive protein as obtained by the method according to claim 1 wherein the protein maintains its chemical identity without being subjected to oxidization or deamidation.

37. A multi-chamber container comprising the lyophilized composition according to claim 35 separately stored from an aqueous fluid for its reconstitution to a parenterally adminsterable fluid.

38. The container according to claim 37 having the lipid and the fluid stored in different chambers separated by at least one movable wall which can be displaced in order to form an injectable fluid just prior to a parenteral administration.

39. The container of claim 38 wherein the movable wall is displaced by an injection device.

40. A method of preparing a composition of lipid particles comprising a lipid agent and a protein, wherein said protein is an apolipoprotein, in hydrophobic interaction comprising:
   (i) introducing protein preparation and a lipid agent, the protein capable of hydrophobic interaction with the lipid agent, to a homogenization station;
   (ii) subjecting resulting fluid mixture of protein and lipid agent to high pressure homogenization at a pressure from about 200 bar to about 2000 bar; and
   (iii) collecting the so formed composition of lipid particles, wherein the protein is not denatured in the preparation of the lipid particles.

41. The method of claim 40 wherein at least one of the following indications of protein denaturation does not occur: aggregation, truncation, deamidation, or oxidation.

* * * * *